US00PP36879P2

(12) United States Plant Patent
Lyrene

(10) Patent No.: US PP36,879 P2
(45) Date of Patent: Aug. 5, 2025

(54) BLUEBERRY PLANT NAMED 'FL16-754'

(50) Latin Name: ***Vaccinium corymbosum* x *Vaccinium stamineum* hybrid**
Varietal Denomination: FL16-754

(71) Applicant: Florida Foundation Seed Producers, Inc., Marianna, FL (US)

(72) Inventor: Paul M. Lyrene, Micanopy, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 18/977,904

(22) Filed: Dec. 11, 2024

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./156, 157
See application file for complete search history.

(56) References Cited

U.S. PATENT DOCUMENTS

PP12,165 P2 10/2001 Lyrene
PP22,778 P3 * 6/2012 Wright ..... A01H 6/368 Plt./157

OTHER PUBLICATIONS

Lyrene, P. 2018. Hybridization of Cultivated Highbush Blueberry with *Vaccinium stamineum*: henotype and Fertility of Backcross 1 populations. HortScience 53: 159-166. (Year: 2018).*

* cited by examiner

*Primary Examiner* — Karen M Redden
(74) *Attorney, Agent, or Firm* — Dentons US LLP

(57) ABSTRACT

A new and distinct hybrid variety of blueberry (*Vaccinium corymbosum* x *Vaccinium stamineum* hybrid), named 'FL16-754', which resulted from an interspecific cross between a highbush blueberry cultivar and a tetraploid plant of *Vaccinium stamineum*. The new blueberry, named 'FL16-754', can be distinguished at least by its a very low chilling requirement for both flower buds and vegetative buds, as well as a vigorous, bushy growth habit. 'FL16-754' berries are borne in loose clusters, with long pedicels and peduncles, with very firm to crisp, medium to large size, with excellent scar. 'FL16-754' is also highly fertile, both as a pollen parent and as a seed parent.

8 Drawing Sheets

Latin name of the genus and species of the plant claimed: *Vaccinium corymbosum* x *Vaccinium stamineum* hybrid.

Variety denomination: 'FL16-754'.

BACKGROUND OF THE INVENTION

The invention relates to a new and distinct hybrid variety of blueberry, named 'FL16-754', which resulted from an interspecific cross between a highbush blueberry cultivar and a tetraploid plant of *Vaccinium stamineum*. *Vaccinium stamineum* is a diploid species native in eastern North America, and because of the strong diploid block in *Vaccinium*, it was necessary to produce tetraploid plants of *V. stamineum* before they could be hybridized with highbush cultivars. This was done by gathering seeds from superior plants of *V. stamineum* growing in a forest near Hawthorne, Florida and treating them with colchicine in 2011. The treated seeds were germinated and the seedlings were grown to the age of flowering. FL 13-1145 was identified as a tetraploid plant in 2013 based on the large size of its pollen tetrads.

In February 2015, to produce interspecific hybrids, flowers of a potted plant of tetraploid southern highbush blueberry clone 'FL12-252', were emasculated before anthesis, and large amounts of freshly-gathered pollen from tetraploid

*Vaccinium stamineum* clone 'FL13-1145' was applied to the stigmas. In November 2015 seeds from the cross were sown in a greenhouse in Gainesville, Florida, and the resulting seedlings were transplanted to a tray of peat in February 2016. In May 2016, one unusually vigorous seedling that showed hybrid characteristics was selected as 'FL16-754'. This plant was transplanted to a 3-gallon pot of peat and grown in the greenhouse through the summer and fall of 2016. The plant flowered in the greenhouse during January and February 2017, and 152 flowers were emasculated and hand pollinated using pollen from tetraploid highbush cultivars to produce berries for evaluation of 'FL16-754'. These pollinations resulted in 109 berries. Because of the high vigor of 'FL16-754' and because its berries were large, juicy, very firm, had excellent picking scar, and exceptionally good flavor, 'FL16-754' was asexually propagated from the original plant by softwood cuttings in June 2017. Clonal plantings of 'FL16-754' were established at Citra, Florida (3 plants in 2018), at Windsor, Florida (15 plants in 2018), and at Fairhope, Alabama (76 plants in 2019). The clone continued to show the hybrid characteristics expected based on the parents. All plantings were vigorous and produced high-quality berries like those of the original plant. At Citra and at Fairhope, 'FL16-754' survived and grew vigorously in fields where many of the surrounding highbush clones died or grew poorly. At Windsor, where conditions were more favorable, both 'FL16-754' and the large array of highbush test selections with which it was planted have remained vigorous and healthy.

SUMMARY OF THE INVENTION

'FL16-754' is the first clone to be presented for patenting that combines genetics from a cultivated highbush blueberry clone and the undomesticated wild blueberry relative, *Vaccinium stamineum*. 'FL16-754' differs from its parents and from blueberry plants of all cultivars. The following are distinguishing characteristics of 'FL16-754' when grown under normal horticultural practices in north-central Florida: (1) a very low chilling requirement for both flower buds and vegetative buds; (2) a vigorous, bushy growth habit with canes 2 to 4 m tall; (3) Average date of 50% anthesis at Citra, Florida is February 28, and the average date of 50% ripe berry is May 15. Both dates are about 20 days later than for the highbush blueberry cultivar Emerald. (4) The ripe berries are borne in loose clusters, with long pedicels and peduncles; (5) Berries are very firm to crisp, medium to large size, with excellent scar. The berries are exceptionally flavorful, with good aroma, high sugar and medium acid; (6) 'FL16-754' is highly fertile, both as a pollen parent and as a seed parent. It produces vigorous, highly-productive hybrid seedlings when crossed with a wide range of tetraploid highbush cultivars. The plant produces partial crops when self pollinated, but yields more berries and larger berries when cross pollinated with pollen from other highbush blueberry cultivars. Evergreen plants of 'FL16-754' grown in a greenhouse produce parthenocarpic berries if the flowers are not pollinated. These are smaller and slower to ripen than berries from pollinated flowers.

'FL16-754' differs from its highbush parent 'FL12-252' in the following ways: (1) the anthers in some of its flowers have short awns. Anther awns are not found in highbush blueberries or in their close relatives (*Vaccinium* species in section *Cyanococcus*). (2) New vegetive shoots are pubescent in 'FL16-754' and glabrous in 'FL12-252'. (3) The upper surface of the leaf has reticulate venation in 'FL16-754' and pinnate in 'FL12-252'. (4) The skin of the ripe berry of 'FL16-754' is thicker than in 'FL12-252', making it seem crunchy. (5) Berries of 'FL16-754' are somewhat smaller than those of 'FL12-252' and more likely to retain the pedicel when picked. (6) Some berries of 'FL16-754' develop internal pigments in the flesh ranging from light pink to dark purple when very ripe; berries of 'FL12-252' maintain internal flesh color of white to green to yellow at similar stages of ripeness. (7) When grown in the field in North Florida, 'FL16-754' flowers and ripens about 3 weeks later than 'FL12-252'.

'FL16-754' differs in many ways from *V. stamineum* clone 'FL13-1145', its pollen parent. The corolla of flowers of 'FL16-754' enclose the anthers and stigma at anthesis, whereas the corollas of 'FL13-1145' are very short, and both anthers and stigmas extend far beyond the corolla aperture; the anther awns of 'FL16-754' are much smaller; the pedicels are much shorter and the berries normally detach without the pedicel when harvested, unlike those of the pollen parent; Softwood cuttings of 'FL16-754' readily produce adventitious roots under mist whereas cuttings of *V. stamineum* are very difficult to propagate from stem cuttings; the berries of 'FL16-754' ripen a month earlier than those of 'FL13-1145'; the skin of ripe berries is bitter in 'FL13-1145' but not in 'FL16-754'.

Blueberry variety 'Emerald' (U.S. Plant Pat. No. 12,165) is planted throughout the southeastern United States and is used here for comparison. Plants of 'FL16-754' can readily be distinguished from 'Emerald' because flowering and ripening is later. The new stems of 'FL16-754' are pubescent and those of 'Emerald' glabrous. 'FL16-754' has small anther awns, and reticulate venation, both of which are lacking in 'Emerald'. The plant architecture of 'FL16-754' is similar to that of 'Emerald'. The berries of 'FL16-754' are firmer, sweeter, and more aromatic than those of 'Emerald' and are borne in looser clusters. 'Emerald' does not develop the pink to purple flesh pigments that develop in some of the ripe berries of 'FL16-754'.

BRIEF DESCRIPTION OF THE DRAWINGS

'FL16-754' is illustrated by the accompanying photographs as described below. The colors shown are as true as can be reasonably captured by conventional photographic procedures.

DETAILED BOTANICAL DESCRIPTION

Figure 1:
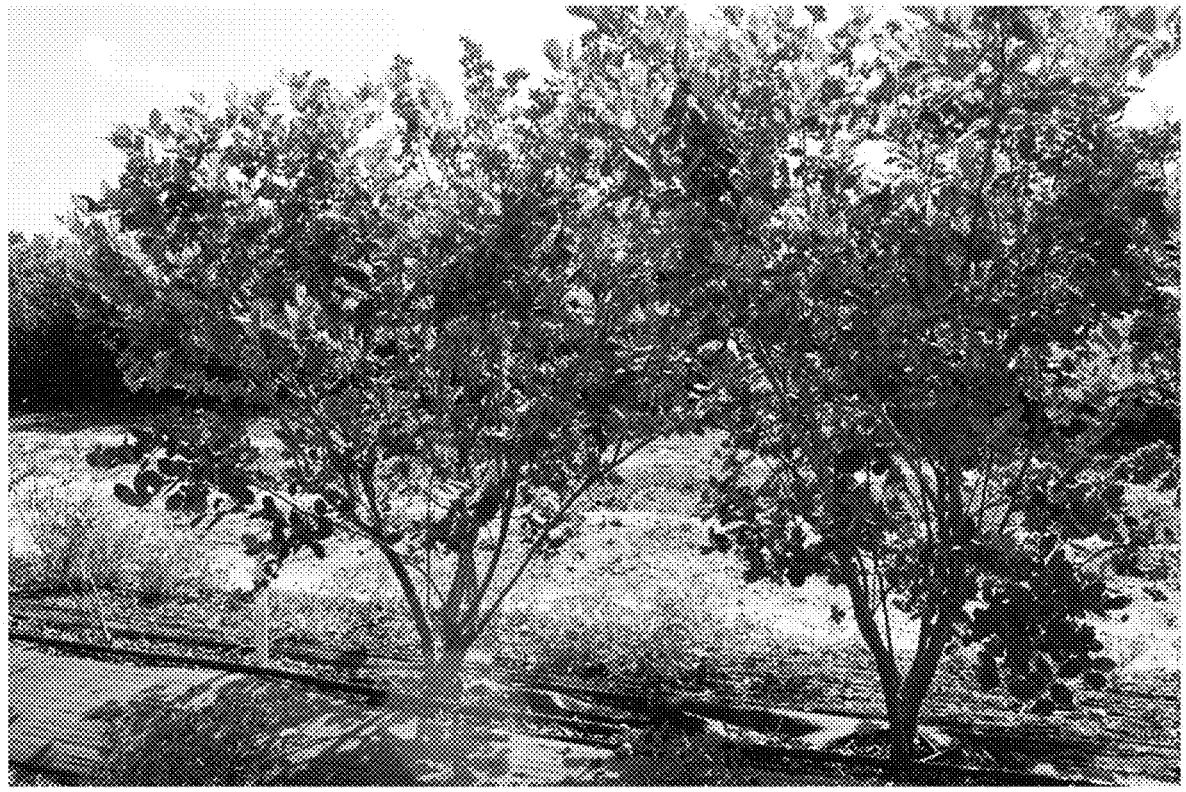
FIG. 1. 'FL16-754' in April of the third-growing season at Citra, showing good leafing and upright, semi-spreading growth habit.
Figure 2:
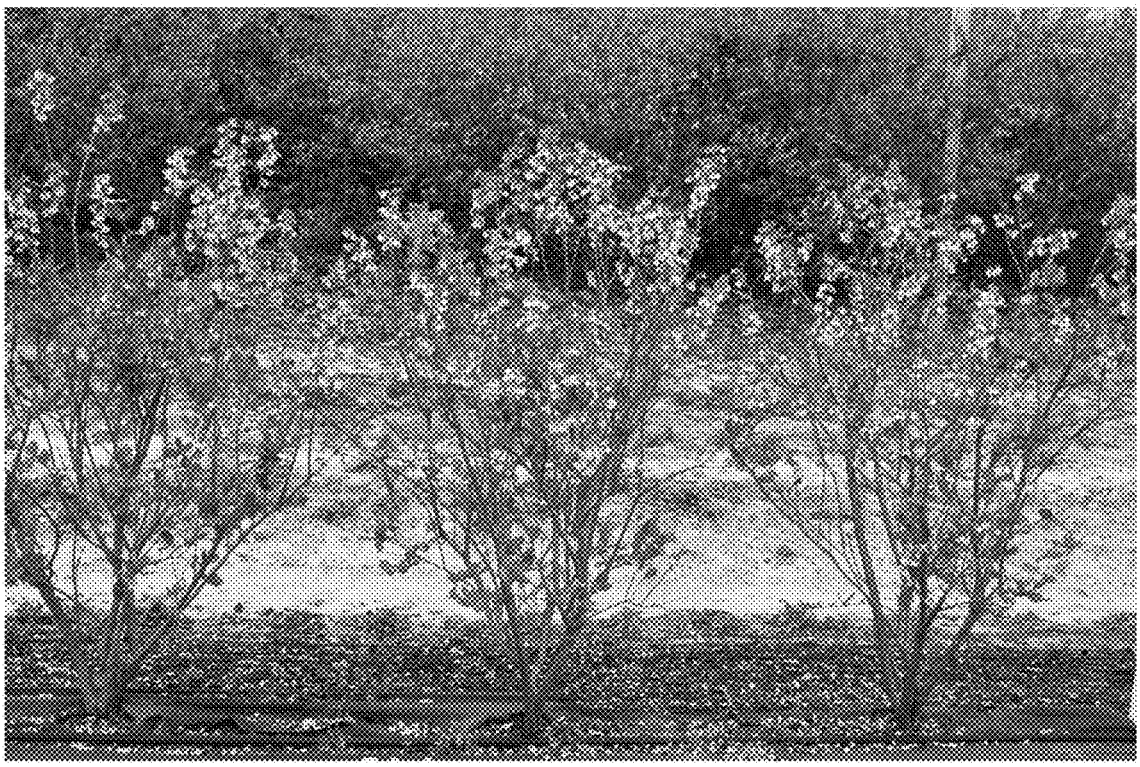
FIG. 2. 'FL16-754' plants at Citra, Florida flowering in late February during their second growing season in the field.
Figure 3:
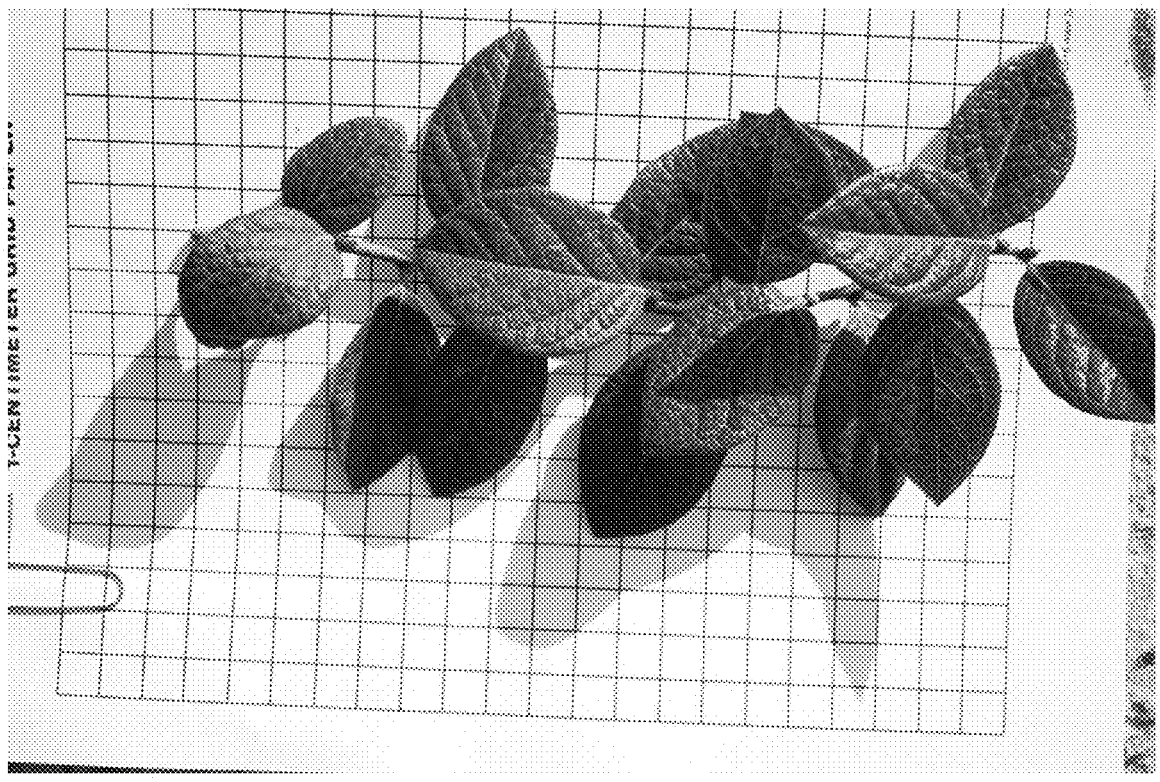
FIG. 3. 'FL16-754' leaves against 1-cm squares showing rugose upper surface of leaves and flower buds developing in late October on three-year-old plants/
Figure 4:
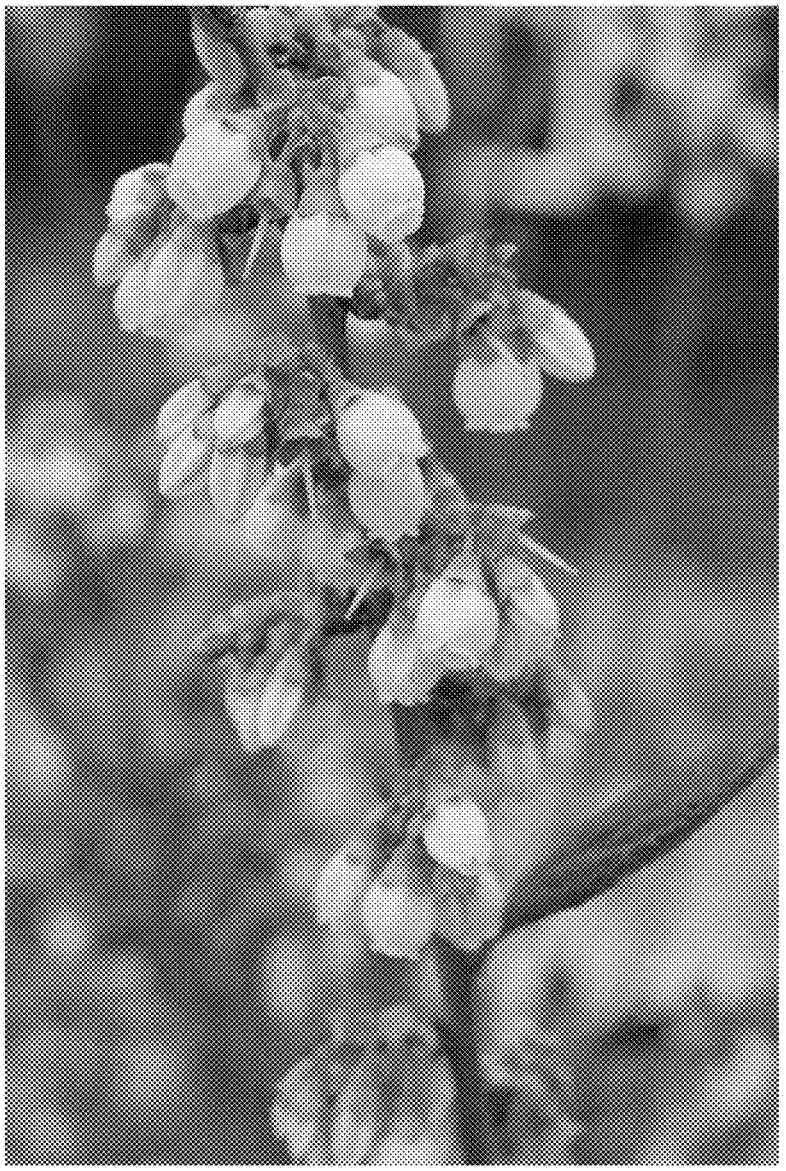
FIG. 4. Flowering branch on three-year-old 'FL16-754' showing wide calyx apertures allowing easy access to pollinating insects.
Figure 5:
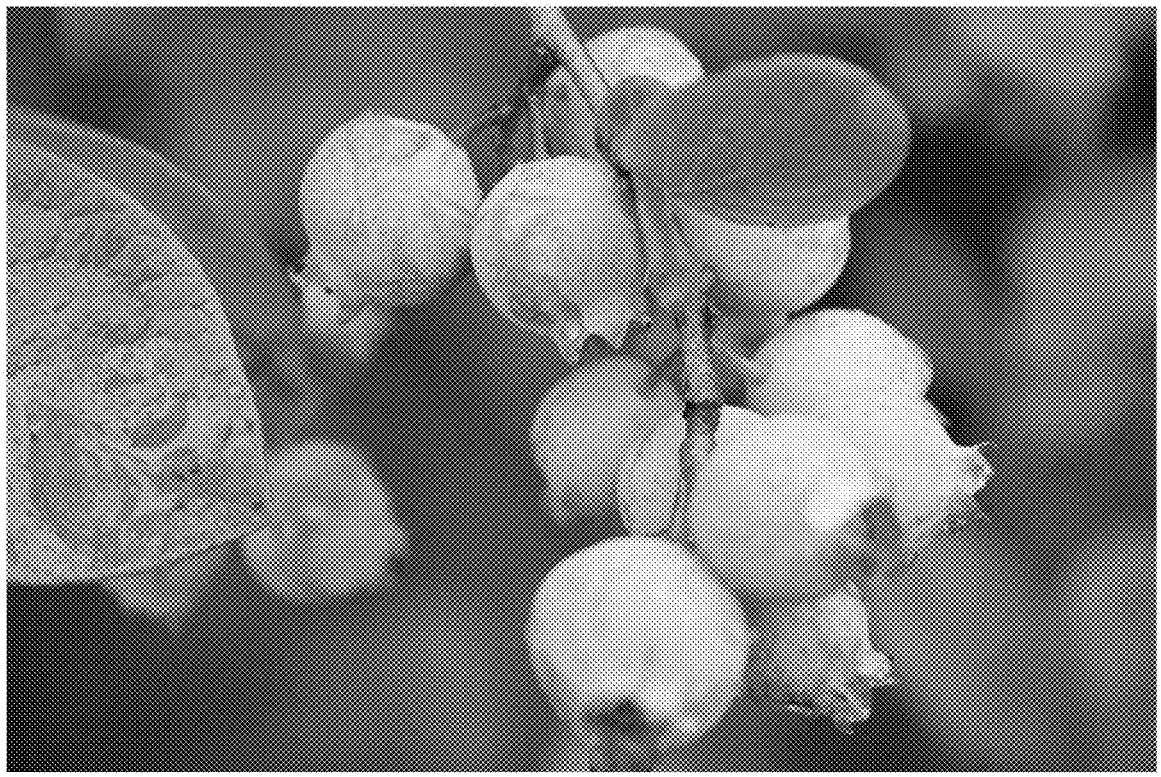
FIG. 5. Immature berries of 'FL16-754' in mid-April showing surface wax and erect calyx lobes.
Figure 6:
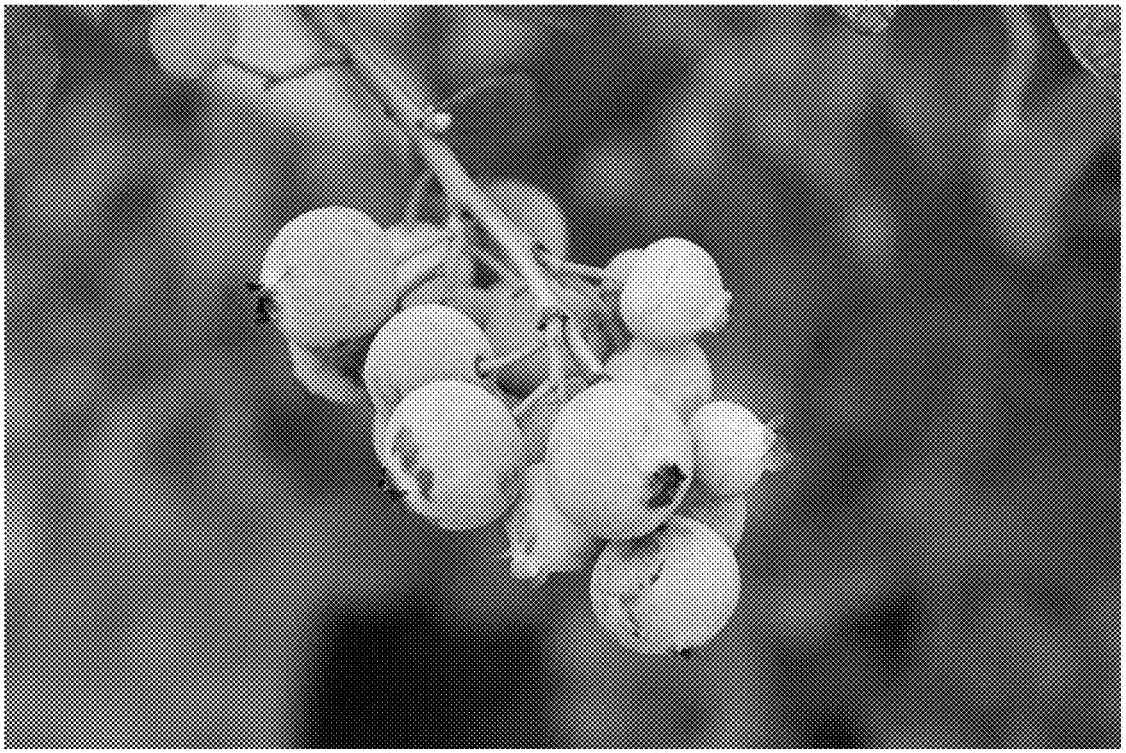
FIG. 6. Ripening berries of 'FL16-754' in early May at Citra showing long pedicels and loose berry clusters.
Figure 7:
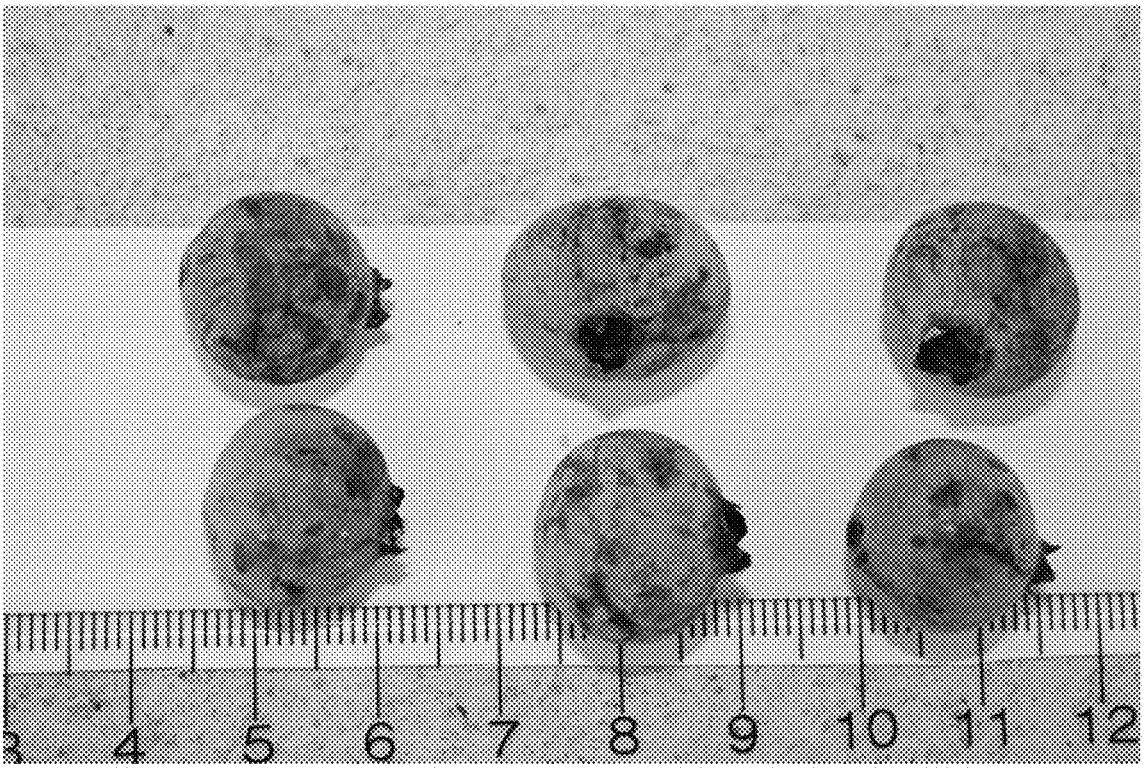
FIG. 7. Ripe berries of 'FL16-754' showing dimensions in cm, surface wax, and erect calyx lobes.
Figure 8:
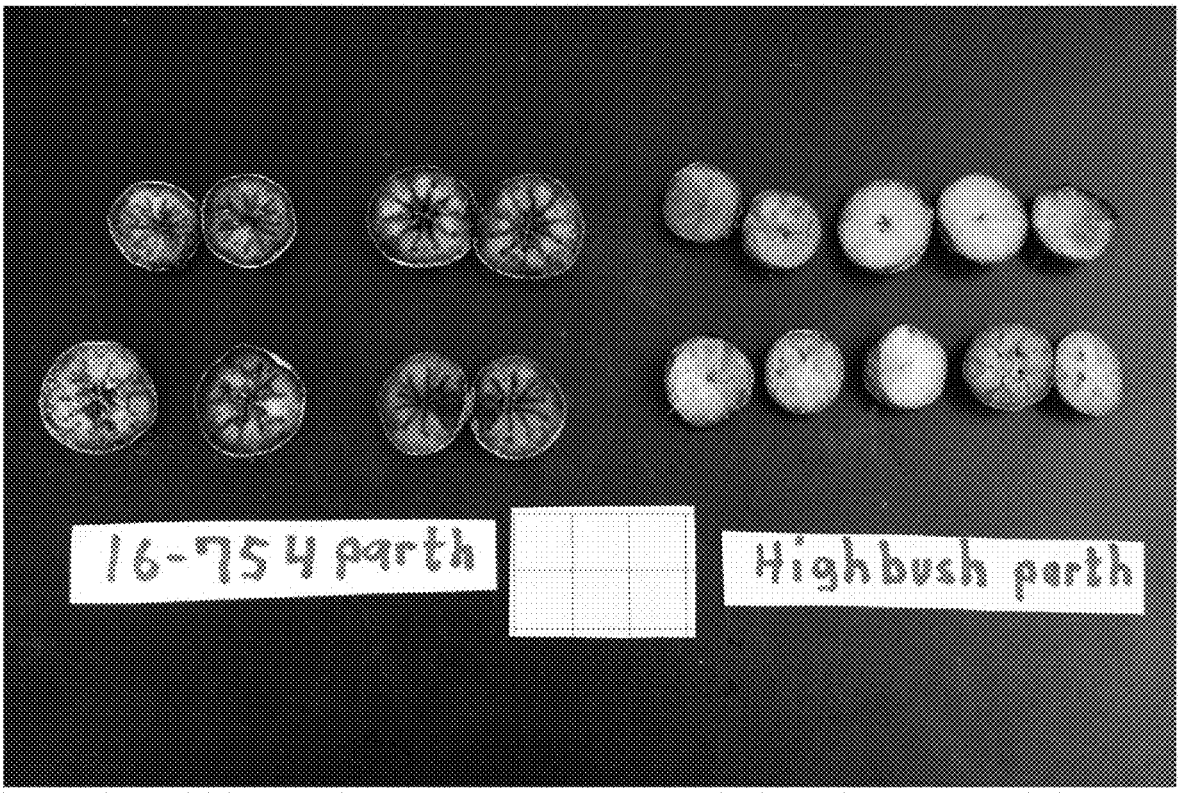
FIG. 8. Ripe berries showing internal pigmentation of parthenocarpic berries of 'FL16-754' compared to normal lack of internal red pigments in highbush cultivars; 1 cm squares.

The following description sets forth distinctive characteristics of 'FL16-754'. The descriptive data were taken from a plot 4-year-old plants growing in a cultivated field at Citra, Florida. The plants had been propagated by softwood stem cuttings from the original seedling. Color descriptions are based on The Pantone Book of Color, by Leatrice Eiseman and Lawrence Herbet, 1990, Harry N. Abrams, Incorporated, New York. Where the Pantone color designations differ from the accompanying photographs, the Pantone designations are accurate.

Classification:

*Family*.—Ericaceae.

*Species*.—An interspecific hybrid between *Vaccinium corymbosum* L. and *Vaccinium stamineum*.

*Common name*.—Southern Highbush Blueberry.

*Cultivar name*.—'FL16-754'.

Plant:

*Plant vigor*.—High.

*Growth habit*.—Bushy to semi-bushy; Round bush architecture; similar to 'Emerald'.

*Plant height*.—2.5 to 3.0 m on 4-year-old unpruned plants.

*Plant diameter*.—1.7 m on 4-year-old unpruned plants.

*Number of inflorescence buds per strong shoots in January*.—6-7.

*Twigginess*.—Low to medium.

*Tendency toward evergreenness*.—Medium.

*Productivity in northeast Florida*.—Kg/season/bush: 5.

*Chilling requirement for best growth*.—(Hours below 7° C.) per winter: 200.

*Plant cold hardiness*.—Medium. Expected to tolerate −10 C° without damage when dormant.

*Ease of propagation*.—Propagates readily from softwood cuttings under mist. Softwood cuttings produced in vitro are expected to root readily under mist. Grows well in nursery pots.

Trunk and branches:

*Suckering tendency*.—Low. Typically makes 3-4 major canes from a basal crown.

*Surface texture of strong, 9-month-old shoots observed in October*.—Smooth.

*Surface texture of 3-year-old and older wood*.—Rough; exfoliating in linear strips.

*Color of current-season shoots observed in the field in September*.—Bright Chartreuse, Pantone 14-0445.

*Color of 3-year-old, rough-textured canes*.—Champagne Beige, Pantone 14-1012.

*Internode length of strong upright shoots measured in September*.—13 mm.

Leaves:

*Leaf color, upper surface*.—Periodot, Pantone 17-0336.

*Leaf color, lower surface*.—Tarragon, Pantone 15-0326.

*Leaf color, petiole*.—Wild Lime, Pantone 13-0540.

*Leaf length including petiole*.—5.5 cm.

*Leaf width at widest point*.—3.3 cm.

*Leaf shape*.—Ovate.

*Leaf base shape*.—Rounded.

*Leaf apex shape*.—Between obtuse and acute.

*Leaf margin*.—Minutely serrate, with marginal hairs and glands.

*Leaf venation pattern*.—Reticulate. The islands delimited by veins are numerous and small compared to those in highbush blueberry.

Pubescence:

*Leaf pubescence, upper surface*.—A high density of white hairs on the midrib and secondary veins; sparse white hairs on the islands between veins.

*Leaf pubescence, lower surface*.—Numerous white, curved hairs on the midrib and secondary veins; A medium density of white hairs on the islands between veins.

*Leaf pubescence, margin*.—Sessile glands present along the margin on the petiolar half of the blade; glandular hairs along the margin of the apical half of the blade.

*Leaf pubescence, petiole*.—Dense pubescence of white hairs along both sides of the petiole.

*Pubescence on young stems*.—Dense covering of short, white hairs.

Phenology:

*Timing of leafing vs flowering without hydrogen cyanamide*.—nearly simultaneous.

*Date of initiation of new vegetative growth in the field at Citra, Florida*.—February 25.

*Date of 10% open flowers at Citra, Florida*.—February 22.

*Date of 50% open flowers*.—February 28 at Citra, Florida. Slightly later than the late-flowering cv Misty. Date of 50% ripe berry at Citra, Florida: May 15.

Flowers:

*Flower fragrance*.—None.

*Flower shape*.—Urceolate. The corolla at anthesis has deep longitudinal grooves and valleys.

*Number of flowers per cluster*.—Average 6.

*Flower cluster density (dense, medium, or loose)*.—Medium to loose.

*Pedicel length at anthesis*.—5 mm.

*Peduncle length at anthesis*.—3 mm.

*Corolla color at anthesis*.—Snow white Pantone 11-0602.

*Anthocyanin coloration in corolla*.—None.

*Calyx color at anthesis*.—Green Olive, Pantone 17-0535.

*Calyx surface texture*.—Smooth.

*Flower pedicel color at anthesis*.—Parrot Green, Pantone 15-0341.

*Corolla length, from pedicel attachment point to end of corolla (excluding the pedicel)*.—12 mm.

*Corolla diameter at widest point*.—9 mm.

*Diameter of corolla aperture*.—5 mm.

*Calyx diameter at anthesis*.—6 mm.

*Style length*.—9 mm.

*Style color*.—Celery Green, Pantone 13-0532.

*Filament length*.—5 mm.

*Filament width*.—2 mm.

*Anther awns*.—2 small awns per anther.

*Location of tip of stigma relative to end of corolla tube*.—Stigma is exserted from 0 to 2 mm beyond the end of the corolla tube depending on which flower is examined.

*Anther color*.—Brown Sugar, Pantone 17-1134.

*Pollen color*.—Antique White, Pantone 11-0105.

*Pollen shed amount*.—High.

*Self-fruitfulness*.—Medium. Flowers that are manually self-pollinated in the greenhouse produce 50 to 100% fruit set. The resulting berries produce viable seed but are smaller and mature later than berries produced by manual cross-pollination. Unpollinated flowers in a greenhouse give high percentage set of seedless berries which are about 70% as large as berries from cross pollination. Parthenocarpic berries mature about a month later than seedy berries produced from pollinated flowers that opened at the same time.

Berry:

*Pedicel length on ripe berry*.—5 to 8 mm, median 7 mm.

*Detachment force of ripe berry*.—(Easy, medium, hard): medium.

*Berry cluster density*.—(Sparse, medium, dense): sparse.

*Number of berries per cluster*.—5.

*Fruiting on*.—Old growth, current growth, or both: both.

*Berry height*.—15 mm.

*Berry width*.—16 mm.

*Berry weight*.—2.01 g.

*Berry shape*.—Urceolate.

*Diameter of the calyx aperture on the mature berry*.—3 mm.

*Size and shape of calyx lobes on mature berries*.—Very small, 1-2 mm long; triangular.

*Calyx lobes*.—Erect.

*Intensity of waxy bloom*.—Medium.

*Surface color of immature berry 3 weeks before color break, unpolished (waxy bloom present)*.—Fog green, Pantone 13-0210.

*Surface color of immature berry 3 weeks before color break, polished to remove wax*.—*Green Glow, Pantone* 13-0442.

*Surface color of mature berry on plant*.—Slate Gray, Pantone 16-5804.

*Surface color of mature berry with wax removed*.—Ebony, Pantone 19-9104.

*Flesh color of berries when first ripe*.—Lily Green, Pantone 13-0317.

*Pedicel scar*.—Very small and dry.

*Berry firmness*.—Very firm to crunchy.

*Berry flavor, overall*.—Sweet with a unique aromatic flavor and medium to low acid.

*Berry flavor*.—Intensity of acidity: low to medium.

*Berry flavor*.—Intensity of sweetness: very sweet.

*Berry flavor*.—Intensity of aromatics: has a pleasant, unusual aromatic flavor.

*Flavor of mature berries that have been dried at room temperature*.—Sweet, no acid, with a slight piney bitterness.

*Berry texture*.—Flesh and skin: the flesh is juicy with small seeds and no grit; the skin is somewhat tougher than normal for highbush blueberry, making the berry seem crunchy when eaten.

*Fruit storage quality*.—Fruit is unusually firm and can be stored without shriveling, mold or loss of firmness for 12 to 16 weeks at 4C.

*Color of dried seeds*.—Burnt Henna, Pantone 19-1540.

*Weight of well-developed dried seeds*.—0.79 mg per seed.

*Length of well-developed dried seeds*.—2.0 mm.

*Width of well-developed dried seeds*.—1.1 mm.

Use: Produces southern highbush blueberries with exceptional flavor and firmness for the fresh market.

Resistance to diseases, insects, and mites: 'FL16-754' has grown vigorously at all three field locations where it has been tested (Alachua County and Marion County in Florida, Baldwin County in Alabama). At two of these locations, 'FL16-754' remained healthy when plants of many other highbush test selections grew poorly or died. When grown with normal practices used to produce highbush blueberries in Florida, 'FL16-754' has not shown unusual problems with insects, mites, or diseases.

What is claimed:

1. A new and distinct bluebuerry plant called 'FL16-754' as illustrated and described herein.

* * * * *